(12) United States Patent
Detmer et al.

(10) Patent No.: US 6,589,177 B1
(45) Date of Patent: Jul. 8, 2003

(54) METHOD AND APPARATUS FOR OBTAINING B-FLOW AND B-MODE DATA FROM MULTILINE BEAMS IN AN ULTRASOUND IMAGING SYSTEM

(75) Inventors: Paul R. Detmer, Seattle, WA (US); James R Jago, Seattle, WA (US); Xiang-Ning Li, Mill Creek, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/295,982

(22) Filed: Nov. 15, 2002

(51) Int. Cl.[7] ................................................. A61B 8/00
(52) U.S. Cl. ....................................... 600/443; 600/455
(58) Field of Search ................................ 600/443, 447, 600/448, 454–456, 449; 367/11; 73/675–676

(56) References Cited

U.S. PATENT DOCUMENTS

| | | | |
|---|---|---|---|
| 4,644,795 A | 2/1987 | Augustine | 73/625 |
| 5,276,654 A | 1/1994 | Mallart et al. | 367/7 |
| 5,546,807 A | 8/1996 | Oxaal et al. | 73/606 |
| 6,102,858 A | 8/2000 | Hatfield et al. | 600/443 |
| 6,104,673 A | 8/2000 | Cole et al. | 367/138 |
| 6,172,939 B1 | 1/2001 | Cole et al. | 367/138 |
| 6,241,674 B1 * | 6/2001 | Phillips et al. | 600/443 |
| 6,241,675 B1 | 6/2001 | Smith et al. | 600/443 |
| 6,276,211 B1 | 8/2001 | Smith | 73/626 |
| 6,277,073 B1 | 8/2001 | Bolorforosh et al. | 600/437 |
| 6,350,240 B1 * | 2/2002 | Song et al. | 600/443 |

* cited by examiner

Primary Examiner—Francis J. Jaworski
Assistant Examiner—Maulin Patel
(74) Attorney, Agent, or Firm—John Vodopia

(57) ABSTRACT

The present invention is a method of and system for imaging an object with an ultrasound transducer array that transmits ultrasound beams and detects echoes reflected from the object. A plurality of adjacent ultrasound beams are transmitted at the object, each of the beams being separated from an adjacent beam by a first predetermined distance. A plurality of groups of echoes are received from the object, with each of the groups of echoes corresponding to one of the plurality of the ultrasound beams. Each of these echoes are spaced from the corresponding ultrasound beam by a second predetermined distance which is less than the first predetermined distance. The transmitted ultrasound beams are arranged such that one of the received echoes corresponding to an ultrasound beam substantially overlaps with one of the received echoes corresponding to an adjacent ultrasound beam. At least a subset of the received echoes are then processed to obtain B-mode data from each of the processed echoes. In addition, the overlapping pairs of received echoes are processed to obtain B-flow data, typically by determining the difference between the overlapping received echoes. Doppler flow data, Doppler power data, and/or Doppler tissue motion data may also be processed from the received echoes.

18 Claims, 4 Drawing Sheets

METHOD AND APPARATUS FOR OBTAINING B-FLOW AND B-MODE DATA FROM MULTILINE BEAMS IN AN ULTRASOUND IMAGING SYSTEM

FIELD OF THE INVENTION

This invention relates to ultrasound imaging systems, and in particular to a system and method for using multiline beams in an ultrasound imaging system to simultaneously obtain both flow and B-mode data, and/or Doppler data (flow, power, and/or tissue motion).

BACKGROUND OF THE INVENTION

Ultrasound scanning systems operate in various imaging modes, depending on the type of image that is desired, the subject being imaged, the constraints of the system itself, etc. The formation of three-dimensional (3D) volumes of ultrasound data in real time strictly limits the number of transmit/receive cycles available for sampling the region to be imaged. The same is true for high frame rate, large field-of-view two-dimensional (2D) applications.

Multiline (or parallel) imaging is a relatively efficient use of transmit cycles because it allows one to obtain multiple receive lines for each transmit event. The basic premise of multiline imaging is to use parallel processing paths to receive multiple beams along adjacent, but spatially distinct, paths from a single transmit event. A single transmit beam is emitted, and parallel beamforming simultaneously receives echo beams along either side (and/or top and bottom for 3D data) of the transmit beam. B-Mode data, which is indicative of the amplitude of the received echoes, may be obtained and displayed (and/or stored) from the received multiline echoes as known in the art. 2×multiline receives one beam on either side of the transmit beam, 4×multiline receives 2 beams on either side, etc. With a 2D array, one can extend the multiline concept into the elevation direction by receiving beam on both sides, top, bottom and diagonally from the transmit beam.

Obtaining flow or motion information requires multiple transmit-receive cycles from the same anatomic region. B-flow imaging is an example of using a minimum number of transmit events (typically two) to obtain flow information. The most straightforward option for producing B-flow images using 2×multiline is to transmit two sequential beams along the same line and then subtract the second pair of received echoes from the first pair of received echoes. This provides the same number of received flow lines as transmit lines and a flow line density that is twice the transmit line density, so it is possible to reduce the transmit line density to compensate for the need to transmit twice down each line. By combining received echoes from addition transmit lines down the same path, this concept can easily be extended to more complex forms of Doppler flow signal processing, such as tissue and blood velocity and power Doppler.

It is desired to be able to optimize ultrasound imaging techniques in order to obtain as much data as possible and provide as much insight as possible regarding a subject being imaged. The present invention addresses this need by providing flow or motion data and B-mode data from the same set of received echoes as explained herein.

SUMMARY OF THE INVENTION

The present invention is directed to an ultrasound imaging system and method that simultaneously forms a B-mode volume and B-flow volume from the same set of transmit beams. When forming 3D volumes, the image data is usually reduced to a lower sampling density than the original image data (typically a maximum of 256 samples in any dimension, given current processing capabilities). Thus, limitations in image quality or flow quality due to tradeoffs for efficiency can be tolerated to some degree.

This invention is possible if the receive lines between two adjacent transmit lines are steered to overlap to a large degree and the transmit beams are broad enough to overlap to some degree, so that there is some degree of spatial coherence. Processing them would then form a B-flow line, with the quality of the flow signal being dependent on the degree of spatial coherence between the two receive lines and the velocity range being dependent on the amount of time between the adjacent transmit cycles, both of which can be controlled by the system design. If more overlapping transmit beams are fired, more complex Doppler processing is possible.

Thus, in a first major aspect of the invention, the present invention is a method of and system for imaging an object with an ultrasound transducer array that transmits ultrasound beams and detects echoes reflected from the object. A plurality of adjacent ultrasound beams are transmitted at the object, each of the beams being separated from an adjacent beam by a first predetermined distance. A plurality of groups of echoes are received from the object, with each of the groups of echoes corresponding to one of the plurality of the transmitted ultrasound beams. Each of these echoes is spaced from the corresponding transmitted ultrasound beam by a second predetermined distance which is less than the first predetermined distance. The transmitted ultrasound beams are arranged such that one of the received echoes corresponding to one transmitted ultrasound beam substantially overlaps with one of the received echoes corresponding to an adjacent transmitted ultrasound beam. At least a subset of the received echoes are then processed to obtain B-mode data from each of the processed echoes. In addition, the overlapping pairs of received echoes are processed to obtain B-flow data, typically by determining the difference between the overlapping received echoes. In a preferred embodiment, each group of echoes comprises a pair of echoes.

In a second major aspect of the invention, the present invention is a method of and system for imaging an object with an ultrasound transducer array that transmits ultrasound beams and detects echoes reflected from the object. A plurality of pairs of adjacent ultrasound beams are transmitted at the object, each of the pairs of beams separated from an adjacent pair of beams by a first predetermined distance. Each pair of beams includes a positive polarity pulse beam and a negative polarity pulse beam, with the positive polarity pulse beam being transmitted in the same space as the negative polarity pulse beam. A plurality of pairs of echoes are received from the object, with each of the pairs of echoes corresponding to one of the plurality of transmitted ultrasound beams. Each pair of echoes includes a first received echo and a second received echo, with each of these echoes spaced from the corresponding transmitted ultrasound beam by a second predetermined distance which is less than the first predetermined distance. The transmitted ultrasound beams are arranged such that one of the received echoes corresponding to one transmitted ultrasound beam substantially overlaps with one of the received echoes corresponding to an adjacent ultrasound beam. At least a subset of the received echoes are then processed to obtain B-mode data from each of the processed echoes. In addition, the overlapping pairs of received echoes are processed to obtain B-flow data. The B-Mode processing utilizes harmonic filtering techniques on the opposite polarity echoes.

Doppler flow data, power data, and/or tissue motion data may also be processed, displayed and/or stored via the data acquisition techniques of this invention.

DETAILED DESCRIPTION OF THE INVENTION

Figure 1:
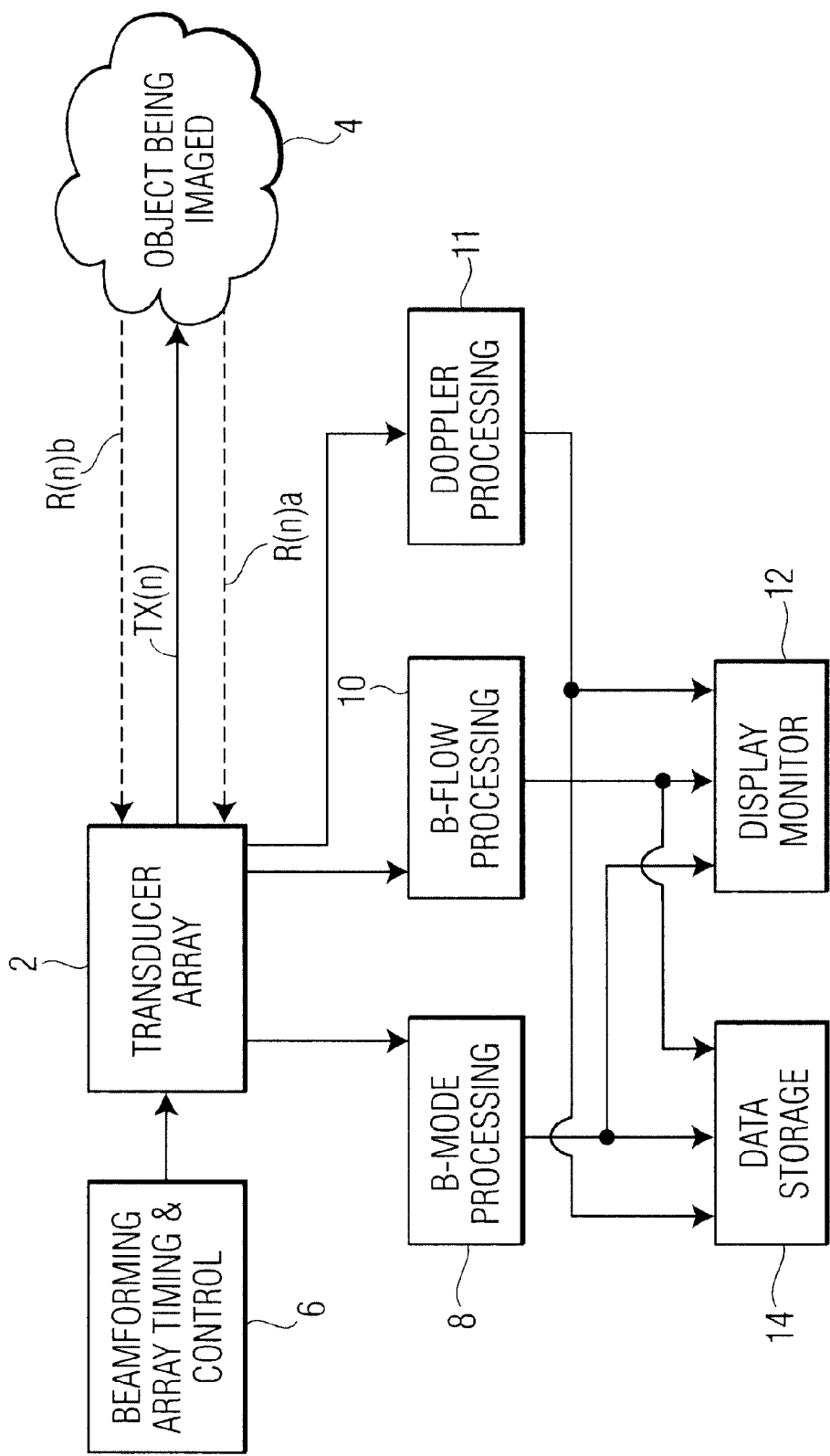
FIG. 1 is a block diagram of the ultrasound system of the preferred embodiment of the present invention.

The preferred embodiment system is shown in FIG. 1. A transducer array 2, which is well known in the art of ultrasound imaging systems, is used to transmit ultrasound beams TX(n) towards the object 4 that is being imaged by the system. The transducer array 2 is also used in a receive mode as well known in the art in order to detect the echoes R(n)a+R(n)b that are received from the object 4 as a result of the transmit beams. The number of transmit events and corresponding receive events (as explained below) is selected based on factors well known in the art, such as the geometry of the transducer array (linear, two-dimensional), the size of the transducer array, the dimensions of the area being imaged (two-dimensional, three-dimensional), etc.

Beamforming/array timing and control logic block 6 is used to control the timing and other parameters of the transmit beams TX(n) in accordance with the present invention. Beamforming techniques known in the art, such as phased array steering and beam shaping techniques, are used for controlling the transducer array 2 in order to generate the transmit beams with the appropriate timing as well as control the transducer array 2 to receive the echoes as explained in detail below.

Two processing logic blocks are utilized in order to implement the present invention: B-Mode processing block 8 and B-Flow processing block 10. As described below, these processing blocks 8, 10 receive as inputs various data streams derived from the transducer array that are then operated on differently by each logic block. That is, B-mode processing block operates on individual echoes, or pairs of echoes (from co-incident transmit beams) for harmonic imaging, to generate B-mode data suitable for display by the display monitor 12 and/or storage in storage means 14, and B-flow processing block operates on pairs of overlapping echoes (from adjacent transmit beams) to generate B-flow data suitable for display by the display monitor 12 and/or storage in storage means 14. By utilizing parallel processing on subsets of the same raw data received by the transducer array 2, the present invention is able to efficiently provide both B-mode fundamental or harmonic and B-flow data on the display simultaneously.

Figure 2:
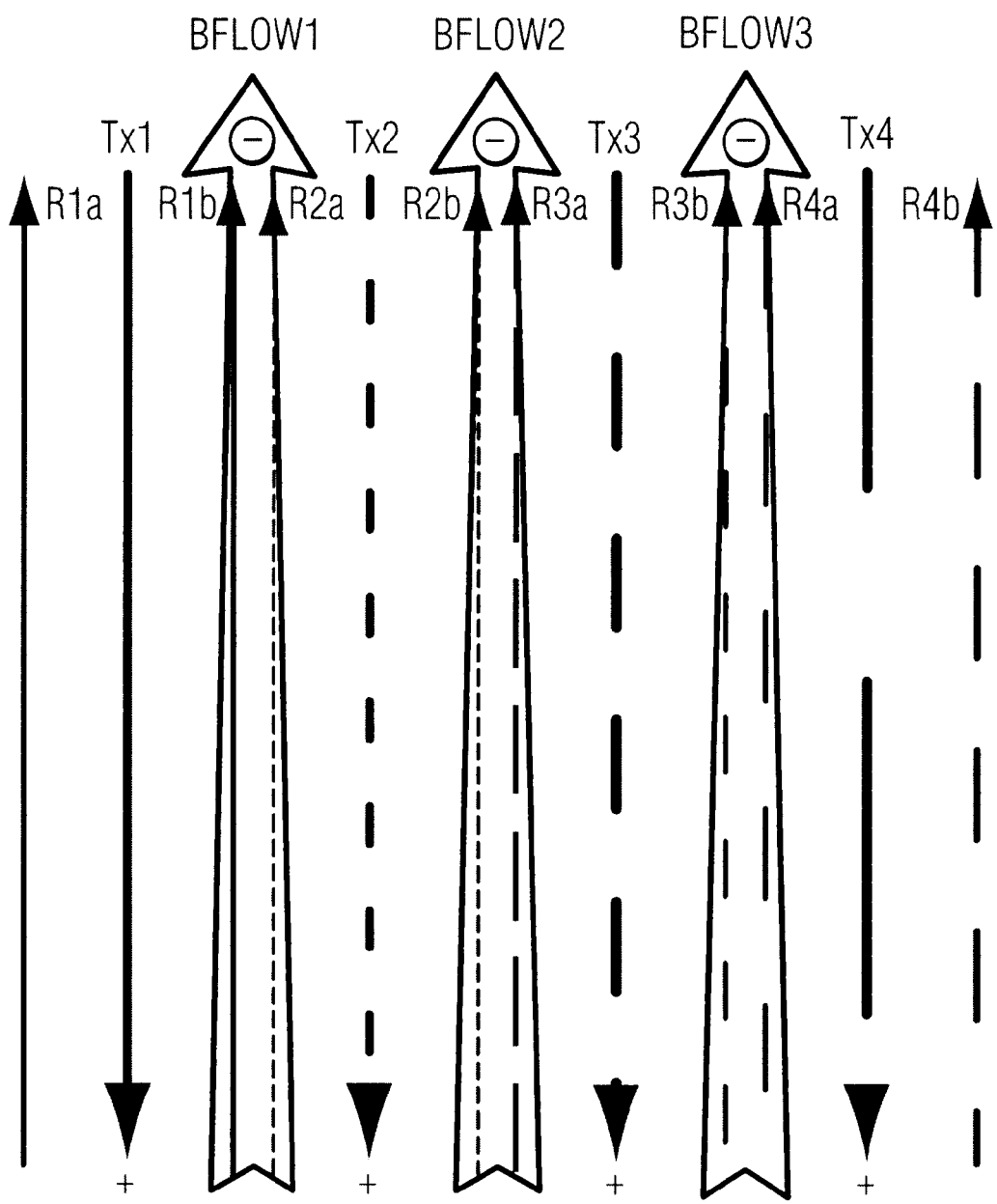
FIG. 2 is an illustration of the transmit events and receive events used to form B-Mode and B-Flow data in the first aspect of the invention.
Figure 3:
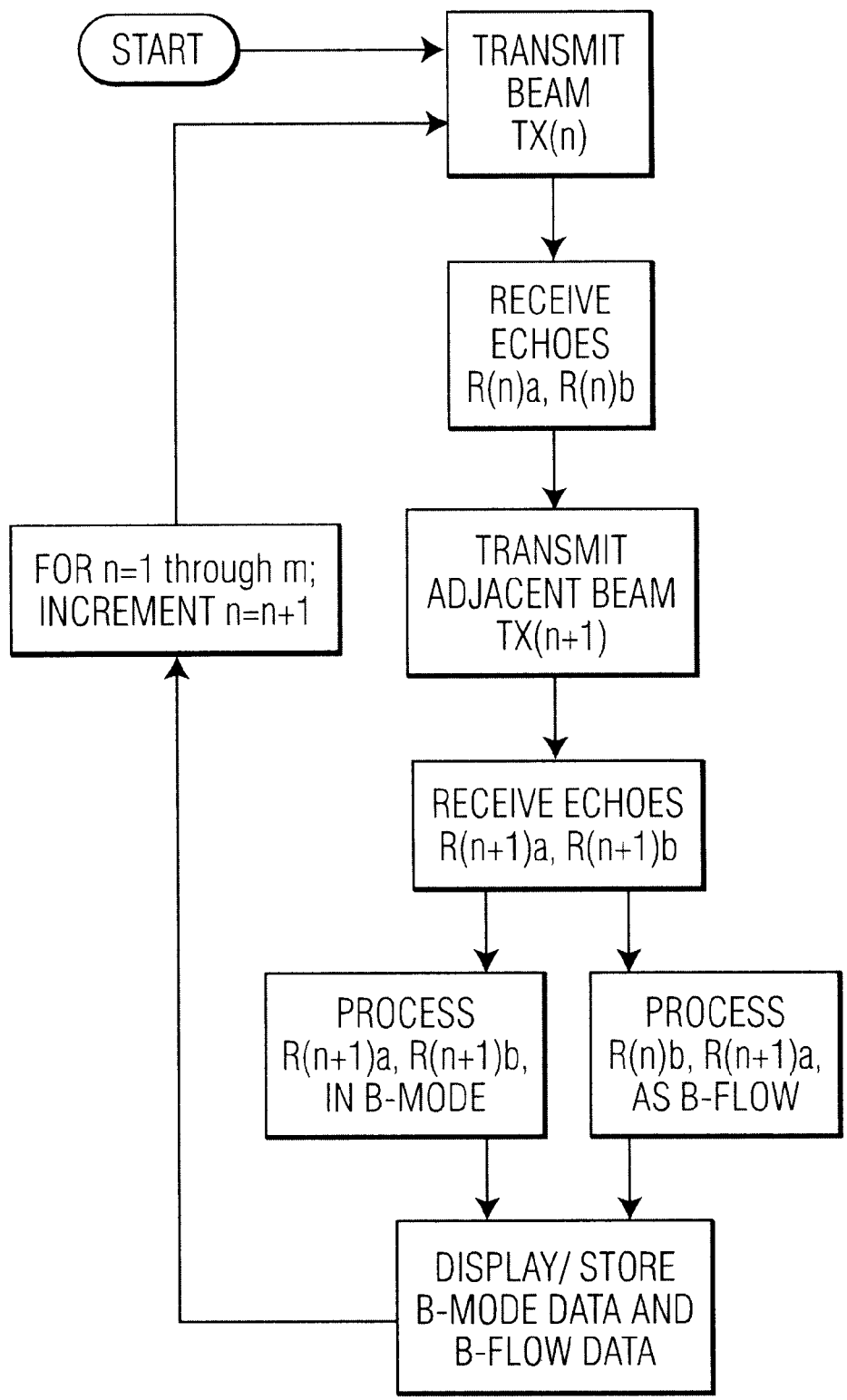
FIG. 3 is a flowchart of the present invention.

With reference to FIGS. 2 and 3, shown is an illustration of the formation of B-flow and B-mode images in accordance with the preferred embodiment of the present invention. A transmit event labeled TX(n) is generated (typically a pulsed beam), and is directed towards the object being imaged. Two receive lines R(n)a and R(n)b are produced by the echoes of TX(n). Similarly, adjacent transmit event TX(n+1) is generated and directed towards the subject, and it provides two receive lines R(n+1)a and R(n+1)b. TX(n+1) is formed so as to be adjacent to TX(n) in a manner such that the beam patterns overlap sufficiently to provide adequate coherence in the receive beams. The distance between TX(n+1) and TX(n) is determined such that receive lines R(n)b (from TX(n)) and R(n+1)a (from TX(n+1)) substantially overlap and can be used to generate a flow signal B-flow(n) by the B-flow processing logic block 10.

Similarly, transmit event TX(n+2) is generated and provides receive lines R(n+2)a and R(n+2)b. Flow signal B-Flow(n+1) is generated from the overlapping receive lines R(n+1)b and R(n+2)a. This pattern is repeated throughout the transducer array to provide m transmit events and 2m receive lines, where m is a number selected by the system designer to provide appropriate resolution given the parameters of the subject being imaged, etc. This logical loop is shown in the flowchart of FIG. 3. The array is generated and processed accordingly, and may take various dimensions and shapes in accordance with the parameters discussed above.

B-mode data is obtained from B-mode processing logic block 8 as shown in FIG. 1. Generation of B-mode data, typically as a function of the amplitudes of the received echoes, is known in the art of ultrasound imaging and need not be discussed in detail here. It is understood that B-mode processing includes such methods as harmonic processing, spatial and frequency compounding and receive processing from coded transmit cycles, as are well known in the art. The system designer may utilize all or various subsets of the raw echo data received from the transducer array as desired (e.g. every received echo may be used, or just every R(n)a echo, or every R(n)b echo, etc).

B-Flow data is likewise obtained from B-Flow processing logic block 10 as shown in FIG. 1. Generation of B-Flow data is generally accomplished by processing overlapping echoes and subtracting the second received echo from the first received echo, such that the difference between the two echoes may be used to extract flow of the object being imaged, for example flow of blood through an artery. Generation of B-Flow data is also known in the art and may be accomplished as such in this invention. What is essential to the present invention is the use of the same data to obtain both B-Mode and B-Flow data as described herein. Once these data sets are generated, each may be displayed on a monitor 12 and/or stored in data storage means 14 for subsequent processing, archival, etc.

The present invention has applicability in three-dimensional imaging as well as two-dimensional imaging described above. That is, the transmit beams TX(n) that are generated across a planar dimension (azimuth) may also be generated at various levels of elevation as known in the art, so as to form a three dimensional volume representation of the object being imaged. Since three-dimensional imaging requires many more transmit/receive events due to the extra dimension being imaged, the present invention provides an advantageously efficient methodology for collecting B-Mode and B-Flow data from the same data sets. Straightforward extensions of this idea to higher orders of multiline processing (i.e. more than two receive beams are acquired and processed for each transmitted beam), either in-plane or out-of-plane, can further improve efficiency.

Figure 4:
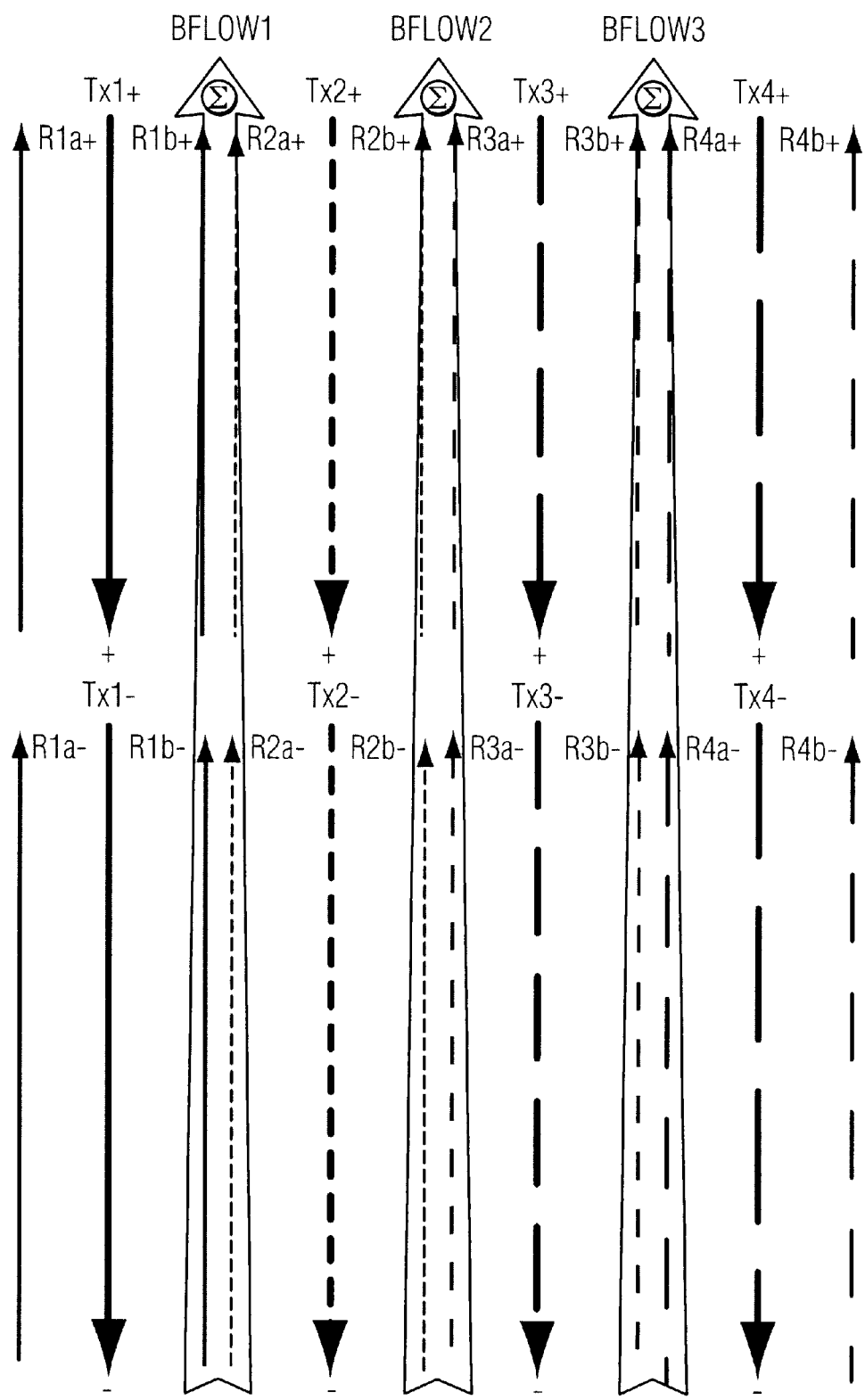
FIG. 4 is an illustration of the transmit events and receive events used to form B-Mode and B-Flow data in the second aspect of the invention.

FIG. 4 illustrates an alternative embodiment of the present invention in which B-flow or normal Doppler processing techniques are combined with pulse inversion harmonic techniques. If the pulse polarity of coincident and/or adjacent transmit beams are inverted, the resulting echoes may be processed to form pulse inversion harmonic images as well as B-Flow images, depending on the filtering that is applied. Two sequential transmit events may be steered down the same position with opposite polarities, and the received echoes may be combined from adjacent transmissions to provide four receive lines. Thus, as shown in FIG. 4, transmit events TX1+ and TX1− are emitted in the same space, one immediately following the other, where TX1+ is a positive polarity pulse and TX1− is a negative polarity pulse. Received multiline echoes R1a+ and R1b+ result from positive polarity pulse TX1+, and R1a− and R1b− result from negative polarity pulse TX1−. Likewise, the next set of adjacent transmit events TX2+ and TX2− generate echoes R2a+ and R2b+, and R2a− and R2b−, respectively. The TX1 echoes may be combined with the TX2 echoes in various ways. For example, if R1b+ and R2a− are combined, the result is a pulse inversion harmonic signal and the B-flow signal as described above. R1a+ and R1b− also provide a pulse inversion harmonic signal, with the difference between R1b− and R2a− resulting in a B-flow signal. Many possible combinations may be made from these data sets in accordance with the teachings of this specification.

In an alternative aspect of the invention, Doppler flow or Doppler power data may be advantageously processed by block 11 in FIG. 1 from the data obtained by the invention. In order to obtain Doppler data, rather than using one transmit line per spatial region as described above for B-flow data, the present invention would cause multiple transmit lines to be sent down each spatial region being imaged and obtain multiple receive lines in accordance with the invention. By recording data from these multiple receive lines (e.g. up to 16 receive lines), Doppler velocity or power data may be advantageously processed to provide blood or tissue motion and flow, strain and power data in accordance with techniques well known in the art.

What is claimed is:

1. A system for imaging an object comprising:
   an ultrasound transducer array for transmitting ultrasound beams and detecting echoes reflected from the object;
   means for controlling the transducer array to transmit a plurality of adjacent ultrasound beams at the object, each of said beams separated from an adjacent beam by a first predetermined distance, and to
   receive a plurality of groups of echoes from the object, each of the groups of echoes corresponding to one of the plurality of ultrasound beams; each of the echoes spaced from the corresponding ultrasound beam by a second predetermined distance which is less than the first predetermined distance; the plurality of transmitted ultrasound beams arranged such that one of the received echoes corresponding to an ultrasound beam substantially overlaps with one of the received echoes corresponding to an adjacent ultrasound beam;
   first processing means for processing at least a subset of the received echoes to obtain B-mode data from each of said processed echoes, and
   second processing means for processing the overlapping pairs of received echoes to obtain B-flow data therefrom.

2. The system of claim 1 wherein the second processing means obtains B-flow data by determining the difference between the overlapping received echoes.

3. The system of claim 2 further comprising means for displaying and storing the B-mode data and the flow data.

4. The system of claim 1 further comprising third processing means for processing the received echoes to obtain data from the group consisting of Doppler flow data, Doppler power data, and Doppler tissue motion data.

5. The system of claim 1 wherein each of said groups of echoes comprises a pair of echoes.

6. A method of imaging an object with an ultrasound transducer array for transmitting ultrasound beams and detecting echoes reflected from the object, comprising the steps of:
   transmitting a plurality of adjacent ultrasound beams at the object, each of said beams separated from an adjacent beam by a first predetermined distance;
   receiving a plurality of groups of echoes from the object, each of the groups of echoes corresponding to one of the plurality of ultrasound beams; each of the echoes spaced from the corresponding ultrasound beam by a second predetermined distance which is less than the first predetermined distance; the plurality of transmitted ultrasound beams arranged such that one of the received echoes corresponding to an ultrasound beam substantially overlaps with one of the received echoes corresponding to an adjacent ultrasound beam;
   processing at least a subset of the received echoes to obtain B-mode data from each of said processed echoes, and
   processing the overlapping pairs of received echoes to obtain B-flow data therefrom.

7. The method of claim 6 wherein the step of processing the overlapping pairs of received echoes to obtain B-flow data determines the difference between the overlapping received echoes.

8. The method of claim 6 further comprising the step of processing the received echoes to obtain data from the group consisting of Doppler flow data, Doppler power data, and Doppler tissue motion data.

9. The method of claim 6 comprising the further step of displaying and storing the B-mode data and the B-flow data.

10. The method of claim 6 wherein each of said groups of echoes comprises a pair of echoes.

11. A system for imaging an object comprising:
   an ultrasound transducer array for transmitting ultrasound beams and detecting echoes reflected from the object;
   means for controlling the transducer array to transmit a plurality of pairs of adjacent ultrasound beams at the object, each of said pairs of beams separated from an adjacent pair of beams by a first predetermined distance, each pair of beams comprising a positive polarity pulse beam and a negative polarity pulse beam, wherein the positive polarity pulse beam is transmitted in the same space as the negative polarity pulse beam, and to receive a plurality of pairs of echoes from the object, each of the pairs of echoes corresponding to one of the plurality of transmitted ultrasound beams; each pair of echoes comprising a first received echo and a second received echo, each of the first received echo and the second received echo spaced from the corresponding ultrasound beam by a second predetermined distance which is less than the first predetermined distance; the plurality of transmitted ultrasound beams arranged such that one of the received echoes corresponding to an ultrasound beam substantially overlaps with one of the received echoes corresponding to an adjacent ultrasound beam;
   first processing means for processing at least a subset of the received echoes to obtain B-mode data from each of said processed echoes, and second processing means for processing the overlapping pairs of received echoes to obtain B-flow data therefrom.

12. The system of claim 11 wherein the first and second processing means comprise means for processing said echoes utilizing harmonic filtering techniques.

13. The system of claim 11 further comprising third processing means for processing the received echoes to obtain data from the group consisting of Doppler flow data, Doppler power data, and Doppler tissue motion data.

14. The system of claim 11 further comprising means for displaying and storing the B-mode data and the flow data.

15. A method of imaging an object with an ultrasound transducer array for transmitting ultrasound beams and detecting echoes reflected from the object, comprising the steps of:

transmitting a plurality of pairs of adjacent ultrasound beams at the object, each of said pairs of beams separated from an adjacent pair of beams by a first predetermined distance, each pair of beams comprising a positive pulse polarity beam and a negative pulse polarity beam, wherein the positive pulse polarity beam is transmitted in the same space as the negative pulse polarity beam;

receiving a plurality of pairs of echoes from the object, each of the pairs of echoes corresponding to one of the plurality of ultrasound beams; each pair of echoes comprising a first received echo and a second received echo, each of the first received echo and the second received echo spaced from the corresponding ultrasound beam by a second predetermined distance which is less than the first predetermined distance; the plurality of transmitted ultrasound beams arranged such that one of the received echoes corresponding to an ultrasound beam substantially overlaps with one of the received echoes corresponding to an adjacent ultrasound beam;

processing at least a subset of the received echoes to obtain B-mode data from each of said processed echoes; and processing the overlapping pairs of received echoes to obtain B-flow data therefrom.

16. The method of claim 15 wherein the processing steps comprise processing said echoes utilizing harmonic filtering techniques.

17. The method of claim 15 further comprising the step of processing the received echoes to obtain data from the group consisting of Doppler flow data, Doppler power data, and Doppler tissue motion data.

18. The method of claim 15 comprising the further step of displaying and storing the B-mode data and the B-flow data.

* * * * *